United States Patent [19]
Francischelli et al.

[11] Patent Number: 5,697,884
[45] Date of Patent: *Dec. 16, 1997

[54] CARDIAC ASSIST DEVICE HAVING CIRCADIAN MUSCLE SIMULATION

[75] Inventors: David Francischelli, Anoka; Kendra K. Gealow, Plymouth; John Hammargren, Medina; Johann J. Neisz, Coon Rapids, all of Minn.

[73] Assignee: Medtronic, Inc., Minneapolis, Minn.

[*] Notice: The term of this patent shall not extend beyond the expiration date of Pat. No. 5,658,237.

[21] Appl. No.: 516,086

[22] Filed: Aug. 17, 1995

[51] Int. Cl.$^6$ .................................. A61N 1/362
[52] U.S. Cl. ............................................ 600/17
[58] Field of Search ........................ 600/16, 17; 607/1, 607/2, 48

[56] References Cited

U.S. PATENT DOCUMENTS

| | | |
|---|---|---|
| 4,411,268 | 10/1983 | Cox . |
| 4,539,993 | 9/1985 | Stanton . |
| 4,735,205 | 4/1988 | Chachques et al. . |
| 4,868,908 | 9/1989 | Pless et al. . |
| 5,098,369 | 3/1992 | Heilman et al. . |
| 5,188,105 | 2/1993 | Keimel . |
| 5,195,518 | 3/1993 | Mannion et al. ............ 607/9 |
| 5,203,326 | 4/1993 | Colins . |
| 5,231,988 | 8/1993 | Wernicke et al. ............ 607/2 |
| 5,251,621 | 10/1993 | Collins ............ 607/6 |
| 5,324,323 | 6/1994 | Bui ............ 600/16 |
| 5,328,442 | 7/1994 | Levine . |
| 5,344,386 | 9/1994 | Schaldach ............ 600/16 |
| 5,354,316 | 10/1994 | Keimel . |
| 5,358,519 | 10/1994 | Grandjean ............ 600/16 |

FOREIGN PATENT DOCUMENTS

0547733A3  6/1993  European Pat. Off. .

OTHER PUBLICATIONS

U.S. Ser. No. 08516415 Francischelli et al. filed Aug. 17, 1995.
U.S. Ser. No. 08516084, Francischelli, filed Aug. 17, 1995.
U.S. Ser. No. 08516082, Neisz, filed Aug. 17, 1995.

(List continued on next page.)

*Primary Examiner*—William E. Kamm
*Assistant Examiner*—George R. Evanisko
*Attorney, Agent, or Firm*—Michael J. Jaro; Harold R. Patton

[57] ABSTRACT

A cardiac assist device having circadian muscle stimulation. In particular the present invention operates in one of two states, either day mode or night mode. During the day mode, muscle stimulation and conditioning are performed according to a first schedule. During the night mode, muscle stimulation and conditioning are performed according to a second schedule. In addition, the night mode is only reached if the night mode is permitted, a set number of sensed beats are less than the night mode rate, and the time of day is nighttime. The night mode is interrupted if the night mode is turned off, the time of day is daytime, or a set number of beats are greater than the night rate. In short, the present invention provides for skeletal muscle stimulation at a less fatiguing level during the night than during the day.

7 Claims, 6 Drawing Sheets

OTHER PUBLICATIONS

U.S. Ser. No. 08516081, Francischelli et al., filed Aug. 17, 1995.

U.S. Ser. No. 08516419, Bourgeois et al., filed Aug. 17, 1995.

Muscle & Nerve, Sep. 1991, p. 850, "Use of a Catchlike Property of Human Skeletal Muscle to Reduce Fatigue" by Stuart A. Binder–Macleod, Phd., PT, and Charles B. Barker III, BS, PT.

J. Cardiovascular and Electrophysiology, V. 6 N. 5 (May 1995), p. 368. "The Effect of Cardiac Compression on Defibrillation Efficacy and the Upper Limit of Vulnerability" by Salim F. Idriss, B.S.E. Mark P. Anstadt, M.D., George L. Anstadt, V.M.D. and Raymond E. Ideker, M.D., Ph.D.

IEEE Transactions on Biomedical Engineering, vol. 42, No. 8, Aug. 1995, "Reducing Muscle Fatigue in FES Applications by Stimulating with N–Let Pulse Trains" by Zoher Z. Karu, William K. Durfee and Aaron M. Barzilai.

Scientific American Science & Medicine, Nov./Dec. 1994, pp. 68–77, "Using Skeletal Muscle for Cardiac Assistance" by Ray C.J. Chiu.

I-592 Circulation, vol. 88, No. 4, Part 2—Oct. 1993, p. 3185, "Cardiac Compression Significantly Improves Defibrillation Efficacy" by Salin F. Idriss, Mark P. Anstadt, George L. Anstadt, Raymond E. Ideker, Duke University Medical Center, Durham, NC.

Japanese Heart Journal, No. 35(I): 73–80, Jan., 1994, "Stroke Volume with Dynamic Cardiomyoplasty during Ventricular Fibrillation in the Acute Dog" by Leslie Alexander Geddes, M.E., Ph.D., Wolfgang Janas, B.Sc., James Cook B.S.E., Marvin Hinds, Ph.D., and Steven Francis Badylak, M.D., Ph.D.

CARDIAC ASSIST DEVICE HAVING CIRCADIAN MUSCLE SIMULATION

FIELD OF THE INVENTION

The present invention generally relates to cardiac assist systems, including cardiomyoplasty, for the treatment of patients needing augmented cardiac output. More specifically, the present invention relates to a cardiac assist system having circadian muscle stimulation.

BACKGROUND OF THE INVENTION

Cardiac assist systems aid patients with chronically and unacceptably low cardiac output who cannot have their cardiac output raised to acceptable levels by traditional treatments, such as drug therapy. One particular type of cardiac assist system currently used is a cardiomyoplasty.

Essentially a cardiomyoplasty provides a muscle-powered cardiac assist system. As seen in U.S. Pat. No. 4,813,952 of Khalafalla, incorporated herein by reference, the cardiomyoplasty is a cardiac assist system powered by a surgically-modified muscle tissue, such as the latissimus dorsi. In particular, the latissimus dorsi is wrapped around the heart. An implantable pulse generator is provided. Implantable pulse generator senses contractions of the heart via one or more sensing leads and stimulates the appropriate nerves of the muscle tissue with burst signals to cause the muscle tissue to contract in synchrony with the heart. As a result, the heart is assisted in its contractions, thereby raising the stroke volume and thus cardiac output. Besides delivering therapeutic electrical pulses to the muscle, the pulse generator is quite often also coupled so as to also provide therapeutic electrical pulses to the heart. See, for example, U.S. Pat. No. 4,735,205 of Chachques et al., incorporated herein by reference.

One problem peculiar to a skeletal muscle powered cardiac assist system is that the skeletal muscle must be conditioned to the constant load of continuous contraction and relaxation demanded of the myocardium. The U.S. Pat. No. 4,411,268 of Cox teaches a technique for conditioning the skeletal muscle. While the apparatus of Cox is effective to accomplish conditioning, his system has no provisions for chronically monitoring the stability of the skeletal muscle following the conditioning process. In practice this necessitates the attention of highly skilled medical personnel to monitor the operation of the skeletal muscle with sophisticated instrumentation and to exercise manual control of the stimulation regimen with pulse generator programming equipment.

As a solution to the inadequate monitoring of the skeletal muscle, Grandjean in U.S. Pat. No. 5,067,960 proposed a system featuring a chronically implantable oximeter positioned within the skeletal muscle. The data from the oximeter is stored within the pulse generator and may be analyzed by a physician to determine the effectiveness of conditioning, the sufficiency of maintenance stimulation, the adequacy of vascularization, and the chronic prognosis for the cardiac assist system. This enabled the physician to manually modify the conditioning regimen upon each visit by the patient to the physician's office. In between each such visit, however, the skeletal muscle was continuously conditioned; no provision was made for the muscle stimulation parameters to be rested at various periods throughout the day.

While past techniques for conditioning the skeletal muscle have proven effective, experimental data suggests continuous conditioning or stimulation may lead to irreversible damage to the muscle. These experiments suggest a period of rest or reduced stimulation may help prevent damage to the muscle. In addition, it is also believed muscle which has been so rested may become, in fact, relatively stronger and thereby may provide a relatively greater amount of assistance to the heart over time as compared to muscle which has undergone constant, unrelenting conditioning or stimulation.

SUMMARY OF THE INVENTION

It is thus an object of the invention to provide a cardiac assist system that permits non-continuous muscle stimulation.

It is a further object of the present invention to provide a cardiac assist system that permits muscle stimulation to be inhibited or the stimulation parameters change at various periods, for example at periods of low-activity or at night.

These and other objects are met by the present invention which comprises a cardiac assist device having circadian muscle stimulation. In particular the present invention operates in one of two states, either day mode or night mode. During the day mode, muscle stimulation and conditioning are performed according to a first schedule. During the night mode, muscle stimulation and conditioning are performed according to a second schedule. In addition, the night mode is only reached if the night mode is permitted, a set number of sensed beats are less than the night mode rate, and the time of day is nighttime. The night mode is interrupted if the night mode is turned off, the time of day is daytime, or a set number of beats are greater than the night rate. In short, the present invention provides for skeletal muscle stimulation at a less fatiguing level during the night than during the day.

BRIEF DESCRIPTION OF THE DRAWINGS

The foregoing and other aspects of the present invention will be best appreciated with reference to the detailed description of the invention in conjunction with the accompanying drawings, wherein.

The drawings are not necessarily to scale.

DETAILED DESCRIPTION OF THE PREFERRED EMBODIMENT

The present invention employs a sensor to monitor cardiac electrical activity and cardiac demand in a skeletal muscle-powered cardiac assist system (hereinafter referred to as "CAS"). A basic CAS may be configured in a variety of ways as described in the aforementioned patent to Khalafalla. One specific configuration is discussed herein simply as an illustration. The present invention, however, may be used in any system concerning cardiac augmentation using skeletal muscle, such as aortic counterpulsation or a skeletal muscle ventricle. Thus it should be understood the particular configuration illustrated is not intended to limit the present invention.

The System of the Present Invention

Figure 1:
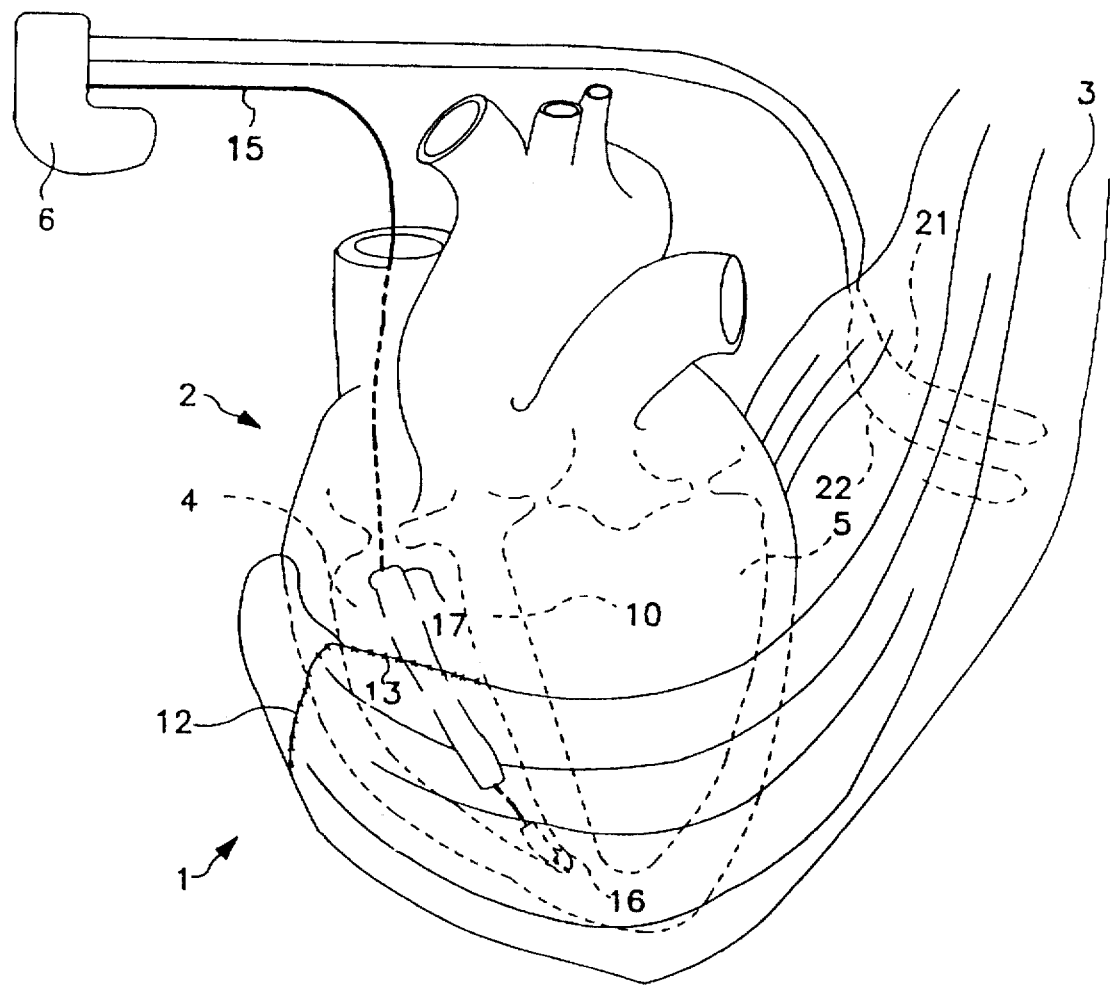
FIG. 1 illustrates an example of a system for performing both long-term stimulation of skeletal muscles for cardiac assistance using systolic augmentation as well as direct electrical stimulation of a heart according to the present invention.

FIG. 1 illustrates an example of a system 1 for performing long-term stimulation of skeletal muscles for cardiac assistance using systolic augmentation as well as direct electrical stimulation of a heart 2. As seen, skeletal muscle graft 3 is positioned about the heart 2. In the preferred embodiment the latissimus dorsi muscle is used for the skeletal muscle graft, as is well known in the art. The longitudinal fibers of the muscle graft 3 are oriented generally perpendicular to the longitudinal axes of the right ventricle 4, left ventricle 5 and interventricular septum 10 of the heart. Muscle graft 3 is positioned in this manner so that when it is stimulated, muscle graft 3 compresses ventricles 4, 5 and particularly left ventricle 5, to thereby improve the force of right and left ventricular contraction. In such a manner the overall hemodynamic output of heart 2 is increased.

In a preferred configuration, muscle graft 3 is wrapped around the heart 2 and fixedly attached to itself to form a cup-shaped "sling," using running sutures 12. Alternatively, muscle graft 3 may be attached to heart 2 using running sutures 13 as illustrated.

As seen, electrical stimulation and sensing of heart 2 is accomplished through lead 15. In particular, lead 15 electrically couples pulse generator 6 to heart 2. Lead 15 provides cardiac pacing as well as defibrillation therapies. In the preferred embodiment lead 15 is the model 6936 tripolar TRANSVENE lead from Medtronic Inc., Minneapolis, Minn. As seen, lead 15 is implanted in right ventricle 4 such that bi-polar pacing electrode assembly 16 is in the right ventricular apex and defibrillation coil 17 is within the right ventricle 4. Although in the preferred embodiment a single lead is provided for pacing as well as defibrillation therapies, other types of lead configurations, such as multiple transvenous or subcutaneous or any combination thereof, may be used.

Muscle graft 3 is electrically stimulated through a pair of leads 21, 22. In particular leads 21, 22 couple pulse generator 6 to skeletal muscle graft 3. In the preferred embodiment leads 21, 22 are the model 4750 intramuscular lead from Medtronic, Inc., Minneapolis, Minn. As seen, each lead 21, 22 extends from pulse generator 6 to latissimus dorsi muscle graft 3. The electrodes (not shown) of each lead 21, 22 are placed to cause muscle graft 3 to contract when electrically stimulated, as is well known in the art. Other types of leads or electrodes, however, may be used, such as epimysial or neuromuscular leads or nerve cuff electrodes.

The Pulse Generator of the Present Invention

Figure 2:
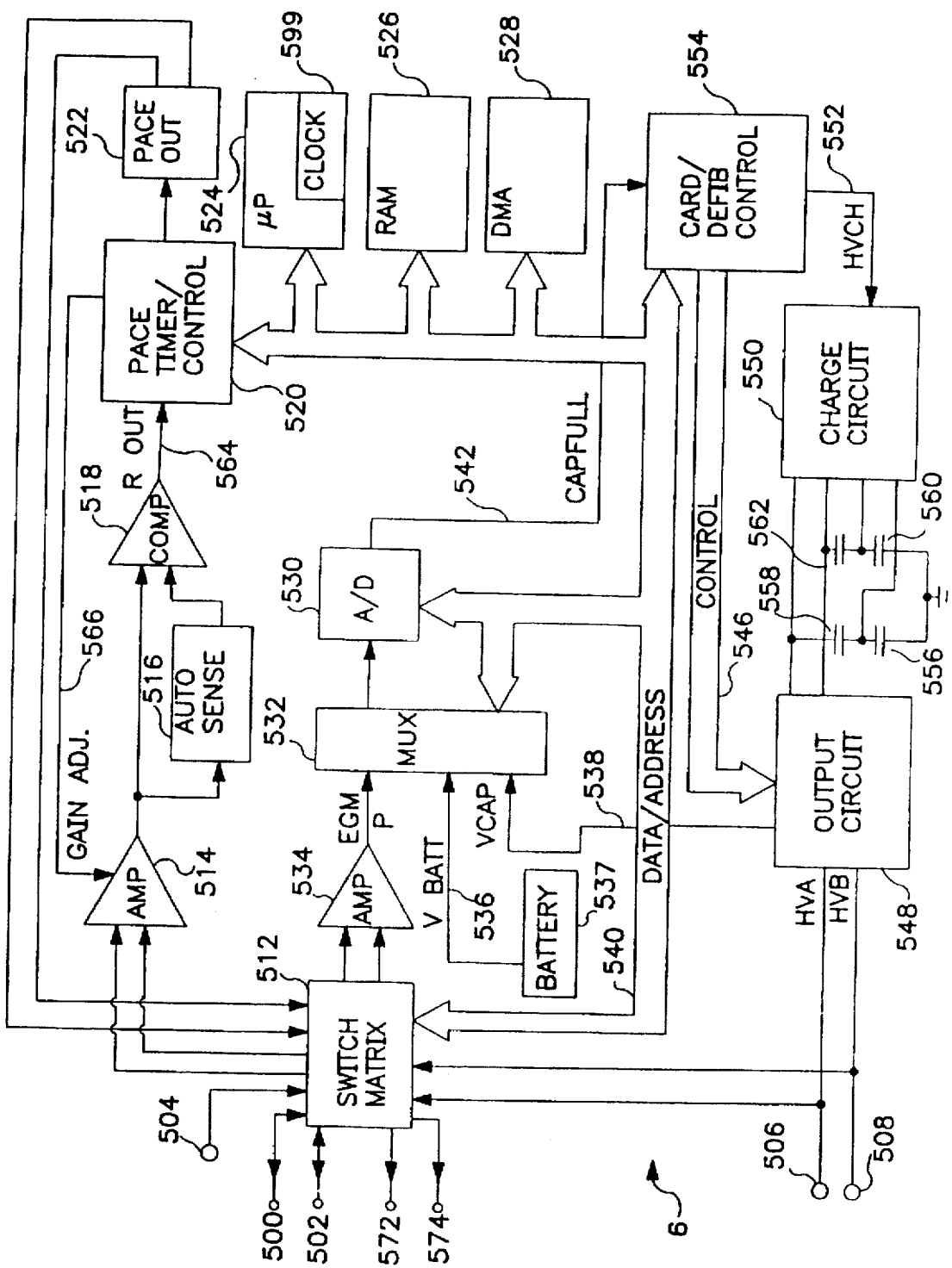
FIG. 2 is a functional schematic diagram of an implantable pulse generator used in the system of the present invention.

FIG. 2 is a functional block diagram of a pulse generator 6 in which the present invention may usefully be practiced. This diagram should only be taken, however, as exemplary of the type of device in which the invention may be embodied and not as limiting. It is believed the invention may usefully be practiced in a wide variety of device implementations. For example, the invention is also believed practicable in conjunction with the implantable muscle stimulator-pacemaker-cardioverters-defibrillators disclosed in U.S. Pat. No. 5,251,621 issued to Collins entitled "Arrhythmia Control Pacer Using Skeletal Muscle Cardiac Graft Stimulation."

The device is illustrated as being provided with six electrodes, 500, 502, 504, 506, 508, 572 and 574. Electrodes 500 and 502 may be a pair of electrodes located in the ventricle and mounted to a lead 15 as discussed above. Electrode 504 may correspond to a remote, indifferent electrode located on the housing of pulse generator 6. Electrodes 506 and 508 may correspond to large surface area defibrillation electrodes located within the right ventricle, coronary sinus, superior vena cava or may also be located subcutaneous, located on or part of the device housing or to the epicardium. Electrodes 572 and 574 are muscle stimulation electrodes coupled to the skeletal muscle wrap 3, as discussed above.

Electrodes 500 and 502 are switchable through switch matrix 512 to the R-wave detector circuit, comprising band-pass filter circuit 514, auto threshold circuit 516 for providing an adjustable sensing threshold as a function of the measured R-wave amplitude and comparator 518. A signal is generated on R-out line 564 whenever the signal sensed between electrodes 500 and 502 exceeds the present sensing threshold defined by the auto threshold circuit 516. As illustrated, the gain on the band pass amplifier 514 is also adjustable by means of a signal from the pacer timing and control circuitry 520 on GAIN ADJ line 566.

The operation of this R-wave detection circuitry may correspond to that disclosed in commonly assigned U.S. Pat. No. 5,118,824, issued to Keimel and incorporated herein by reference. However, alternative R-wave detection circuitry such as that illustrated in U.S. Pat. No. 4,819,643, issued to Menken and U.S. Pat. No. 4,880,004, issued to Baker et al., both incorporated herein by reference, may also be employed.

The threshold adjustment circuit 516 sets a threshold corresponding to a predetermined percentage of the amplitude of a sensed R-wave, which threshold decays to a minimum threshold level over a period of less than three seconds thereafter, similar to the automatic sensing threshold circuitry illustrated in the article "Reliable R-Wave Detection from Ambulatory Subjects", by Thakor et al., published in Biomedical Science Instrumentation, Vol. 4, pp. 67–72, 1978.

It is preferable that the threshold level not be adjusted in response to paced R-waves, but instead should continue to approach the minimum threshold level following paced R-waves to enhance sensing of low level spontaneous R-waves associated with tachyarrhythmias. The time constant of the threshold circuit is also preferably sufficiently short so that minimum sensing threshold may be reached within 1-3 seconds following adjustment of the sensing threshold equal to 70–80% of the amplitude of a detected spontaneous R-wave. The invention may also be practiced in conjunction with more traditional R-wave sensors of the type comprising a band pass amplifier and a comparator circuit to determine when the band-passed signal exceeds a predetermined, fixed sensing threshold.

Switch matrix 512 is used to select which of the available electrodes are coupled to band pass amplifier 534. Under control of microprocessor 524, switch matrix directs delivery of electrical stimulation pulses to cardiac tissue and the skeletal muscle wrap. Selection of the switch matrix settings is controlled by the microprocessor 524 via data/address bus 540. Signals from the selected electrodes are passed through band-pass amplifier 534 and into multiplexer 532, where they are convened to multi-bit digital signals by A/D converter 530, for storage in random access memory 526 under control of direct memory address circuit 528. Multiplexer 532 further receives voltage from battery 537 via VBATT 536.

Amplifier 534 may be a broad band pass amplifier, having a band pass extending for approximately 0.5 to 200 hertz. The filtered EGM signals from amplifier 534 are passed through multiplexer 532, and digitized in A-D converter circuitry 530. The digitized data may be stored in random access memory 526 under control of direct memory address circuitry 528.

The occurrence of an R-wave detect signal on line 564 is communicated to microprocessor 524 via data/address bus 540, and microprocessor 524 notes the time of its occurrence.

The remainder of the circuitry is dedicated to the provision of muscle stimulation, cardiac pacing, cardioversion and defibrillation therapies. The pacer timing/control circuitry 520 includes programmable digital counters which control the basic time intervals associated with cardiac pacing and muscle stimulation. The durations of these intervals are determined by microprocessor 524, and are communicated to the pacing circuitry 520 via address/data bus 540. Pacer timing/control circuitry also determines the amplitude of the muscle stimulation and cardiac pacing pulses and the gain of band-pass amplifier, under control of microprocessor 524.

During cardiac pacing or muscle stimulation, the escape interval counter within pacer timing/control circuitry 520 is reset upon sensing of an R-wave as indicated by a signal on line 564, and on timeout triggers generation of a pacing pulse by pacer output circuitry 522, which is coupled to electrodes 500 and 502 or electrodes 572 and 574. The escape interval counter is also reset on generation of a cardiac pacing pulse, and thereby controls the basic timing of cardiac pacing functions, including anti-tachycardia pacing and subsequent muscle stimulation. The duration of the interval deemed by the escape interval timer is determined by microprocessor 524, via data/address bus 540. The value of the count present in the escape interval counter when reset by sensed R-waves may be used to measure the duration of R-R intervals, to detect the presence of tachycardia and change muscle stimulation parameters.

Microprocessor 524 operates as an interrupt driven device, and responds to interrupts from pacer timing/control circuitry 520 corresponding to the occurrence of sensed R-waves and corresponding to the generation of cardiac pacing and muscle stimulation pulses. These interrupts are provided via data/address bus 540. Any necessary mathematical calculations to be performed by microprocessor 524 and any updating of the values or intervals controlled by pacer timing/control circuitry 520 and switch matrix 512 take place following such interrupts.

In the event that a tachyarrhythmia is detected, and an antitachyarrhythmia pacing regimen is desired, appropriate timing intervals for controlling generation of anti-tachycardia pacing therapies are loaded from microprocessor 524 into the pacer timing/control circuitry 520 and switch matrix 512.

Similarly, in the event that generation of a cardioversion or defibrillation pulse is required, microprocessor 524 employs the counters in timing and control circuitry 520 to control timing of such cardioversion and defibrillation pulses, as well as timing of associated refractory periods during which sensed R-waves are ineffective to reset the timing circuitry.

Further, in the event the onset of a tachyarrhythmia is detected, but not yet confirmed, the filtered and digitized EGM available at A/D 530 will be compared by microprocessor 524 with a value from RAM 526. Measured values above set will continue detection. Values below set confirm the arrhythmia if more than 50% of the X out of Y have been detected. In the preferred embodiment X and Y are programmable counts corresponding to the VFNID and the fibrillation event buffer memory (located in the RAM 526) respectively, both of which are discussed in more detail below with regards to the VF counting mode state 34 seen in FIG. 4. Microprocessor 524 will then initiate a therapy if programmed to do so.

In response to the detection of fibrillation or a tachycardia requiring a cardioversion pulse, microprocessor 524 activates cardioversion/defibrillation control circuitry 554, which initiates charging of the high voltage capacitors 556, 558, 560 and 562 via charging circuit 550, under control of high voltage charging line 552. During charging, microprocessor 524 enables pacer/timing control 520 to pace out 522 and switch matrix 512 to deliver muscle stimulation pulses until the high voltage capacitors 556 are sufficiently charged. The voltage on the high voltage capacitors is monitored via VCAP line 538, which is passed through multiplexer 532, and, in response to reaching a predetermined value set by microprocessor 524, results in generation of a logic signal on CAP FULL line 542, terminating charging. The CAP FULL line 542 signal is sent over DATA/ADDRESS 540 to the pace timer/control 520, which then inhibits delivery of the muscle stimulation pulses.

Thereafter, delivery of the timing of the defibrillation or cardioversion pulse is controlled by pacer timing/control circuitry 520. One embodiment of an appropriate system for delivery and synchronization of cardioversion and defibrillation pulses, and controlling the timing functions related to them is disclosed in more detail in the commonly assigned U.S. Pat. No. 5,188,105 by Keimel, Method and Apparatus for Detecting and Treating a Tachyarrhythmia, incorporated herein by reference. Any known cardioversion or defibrillation pulse generation circuitry, however, is believed usable in conjunction with the present invention. For example, circuitry controlling the timing and generation of cardioversion and defibrillation pulses as disclosed in U.S. Pat. No. 4,384,585, issued to Zipes, in U.S. Pat. No. 4,949,719 issued to Pless et al., cited above, and in U.S. Pat. No. 4,375,817, issued to Engle et al., all incorporated herein by reference may also be employed. Similarly, known circuitry for controlling the timing and generation of anti-tachycardia pacing pulses as described in U.S. Pat. No. 4,577,633, issued to Berkovits et al., U.S. Pat. No. 4,880,005, issued to Pless et al., U.S. Pat. No. 7,726,380, issued to Vollmann et al. and U.S. Pat. No. 4,587,970, issued to Holley et al., all of which are incorporated herein by reference may also be used.

In modern cardiac pulse generators, the particular anti-tachycardia and defibrillation therapies are programmed into the device ahead of time by the physician, and a menu of therapies is typically provided. For example, on initial detection of tachycardia, an anti-tachycardia pacing therapy may be selected. On re-detection of tachycardia, a more aggressive anti-tachycardia pacing therapy may be scheduled. If repeated attempts at anti-tachycardia pacing therapies fail, a higher level cardioversion pulse therapy may be selected thereafter. Prior art patents illustrating such pre-set therapy menus of antitachyarrhythmia therapies include the above-cited U.S. Pat. No. 4,830,006, issued to Haluska, et al., U.S. Pat. No. 4,727,380, issued to Vollmann et al. and U.S. Pat. No. 4,587,970, issued to Holley et al. The present invention is believed practicable in conjunction with any of the known antitachycardia pacing and cardioversion therapies, and it is believed most likely that the invention of the present application will be practiced in conjunction with a device in which the choice and order of delivered therapies is programmable by the physician, as in current cardiac pulse generators.

In addition to varying the therapy delivered following a failed attempt to terminate a tachyarrhythmia, it is also known that adjustment of detection criteria may be appropriate. For example, adjustment may comprise reducing the number of intervals required to detect a tachyarrhythmia to allow a more rapid redetection or by changing the interval ranges to bias detection towards detection of ventricular fibrillation, for example as disclosed in U.S. Pat. No. 4,971,058, issued to Pless et al and incorporated herein by reference.

In the present invention, selection of the particular electrode configuration for delivery of the cardioversion or defibrillation pulses is controlled via output circuit 548, under control of cardioversion/defibrillation control circuitry 554 via control bus 546. Output circuit 548 switches the high voltage electrodes 506 and 508 for delivery of the defibrillation or cardioversion pulse regimen, and may also be used to specify a multi-electrode, simultaneous pulse regimen or a multi-electrode sequential pulse regimen. Monophasic or hipbasic pulses may be generated. One example of circuitry which may be used to perform this function is set forth in U.S. Pat. No. 5,163,427, issued to Keimel, incorporated herein by reference. However, output control circuitry as disclosed in U.S. Pat. No. 4,953,551, issued to Mehra et al. or U.S. Pat. No. 4,800,883, issued to Winstromboth incorporated herein by reference, may also be used in the context of the present invention. Alternatively single monophasic pulse regimens employing only a single electrode pair according to any of the above cited references which disclose implantable cardioverters or defibrillators may also be used.

Operation of the System of the Present Invention

Figure 3:
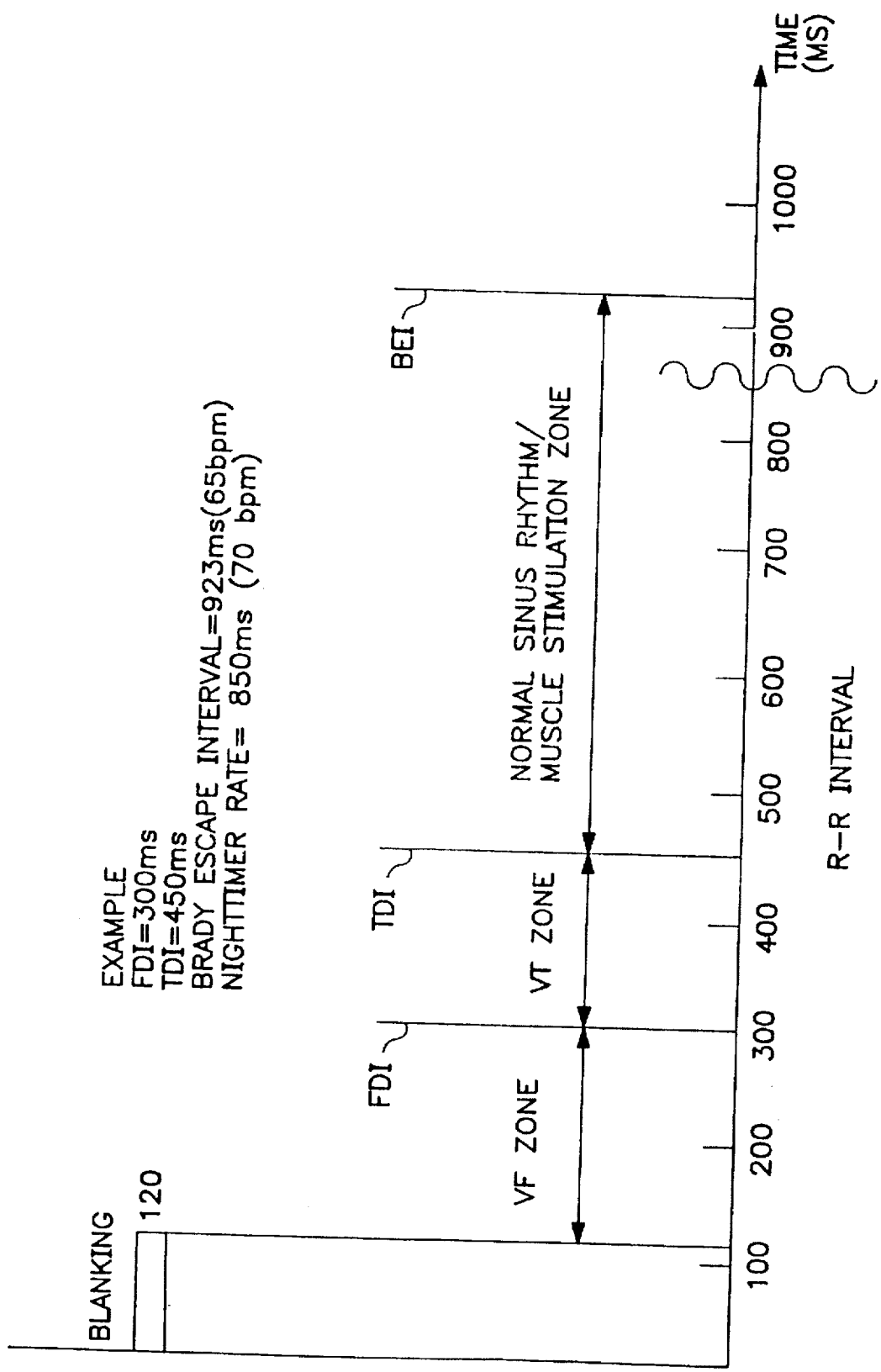
FIG. 3 is an illustration of detection interval ranges employed in a preferred embodiment of the present invention.

FIG. 3 is an illustration of detection interval ranges which may be employed in a preferred embodiment of the present invention. The specific detection interval ranges are selected and programmed by the physician. As seen, events which occur less than 120 milliseconds (hereafter "ms") apart are not detected due to blanking. This is a fixed interval and its length is not programmable by the physician. The range of intervals between detected events taken as indicative of fibrillation are greater than 120 ms and less than 300 ms. That is the fibrillation detection interval (hereafter "FDI") extends to 300 ms. This range is programmed and is selected by the physician to suit the particular patient. The range of intervals between detected events taken as indicative of tachyarrhythmia are greater than 300 ms and less than 450 ms. That is the tachyarrhythmia detection interval (hereafter "TDI") extends to 450 ms. This range is also programmed and is selected by the physician to suit the particular patient. Events having intervals between 450 ms to 923 ms, in the preferred embodiment, are taken as indicative of normal sinus rhythm. That is the brady escape interval (hereafter "BEI") extends to 923 ms. This range is also programmed and is selected by the physician to suit the particular patient. Events which occur at intervals which would be greater than the BEI are taken as indicative of bradycardia.

For example, if a first event is sensed and a second event is sensed 200 ms later, ventricular fibrillation is provisionally detected. As a second example, if a first event is sensed and second event occurs 100 ms later and a third event occurs 210 ms after the second event, then a ventricular tachycardia (hereafter "VT") is provisionally detected. This is so because the second event occurred during blanking and thus was not sensed; the third event was thereafter sensed a sum of 320 ms after the first, well within the VT zone.

It should be noted that the specific times for intervals is for the preferred embodiment and thus is only illustrative of the present invention. Other interval lengths may also be used within the scope of the present invention.

Figure 4:
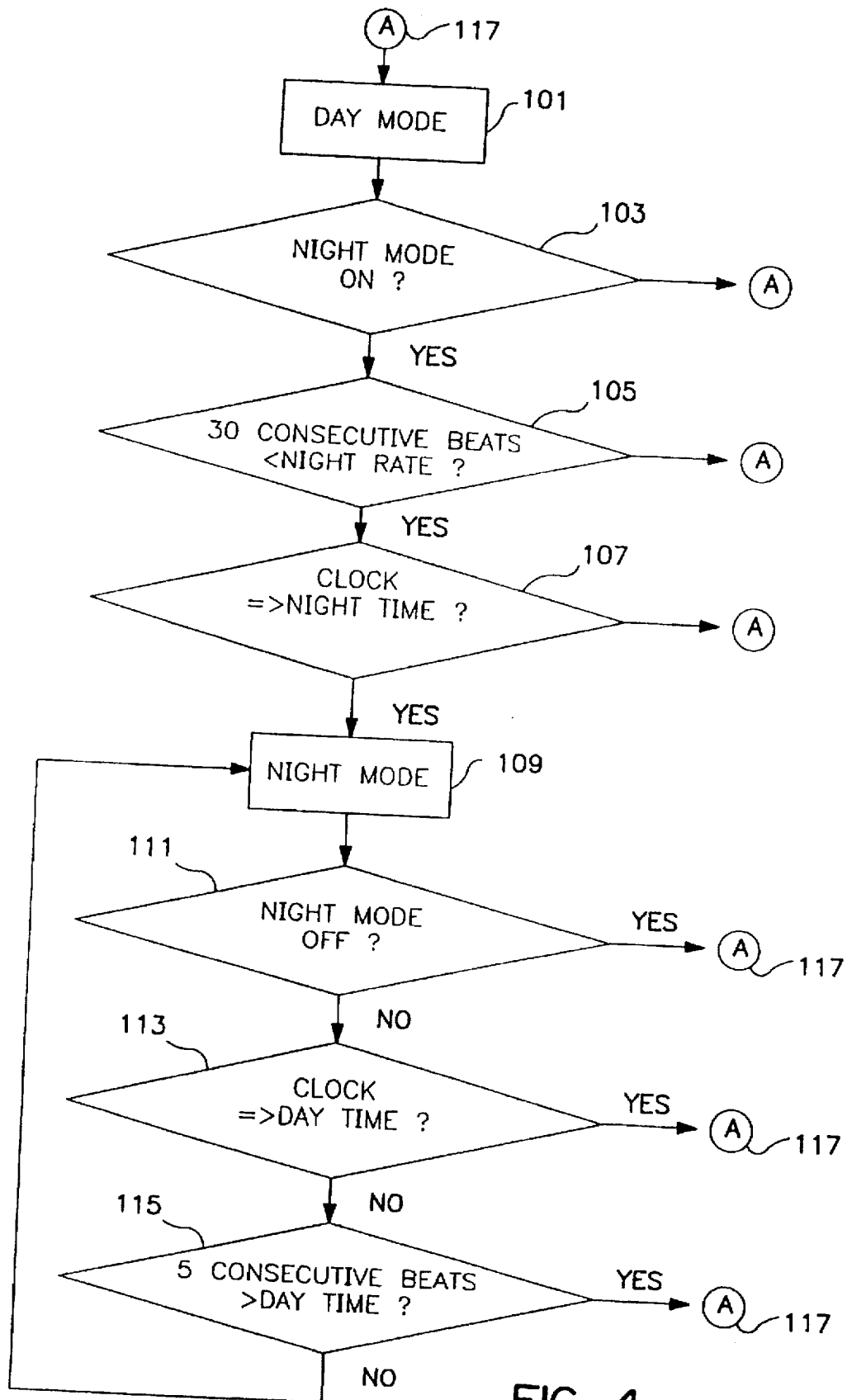
FIG. 4 is a flowchart of the present invention.

FIG. 4 is a flowchart of the present invention. As seen, device begins in the day mode 101. While in day mode 101 device stimulates the muscle according to a predefined schedule. In the preferred embodiment the predefined schedule during day mode 101 is a programmed set of stimulation and detection parameters for muscle stimulation. In an alternate embodiment the predefined schedule during day mode 101 may be a table of values set such that the muscle stimulation and detection parameters gradually change or over time as the patient makes the transition from night to day. At 103 device checks to determine whether night mode has been turned on. If not, device proceeds to block 117. If night mode is on, device proceeds to block 105, where it determines whether 30 consecutive beats have occurred which are less than the night rate. It should be understood, however, that the use of 30 for consecutive beats less than the night rate is only an arbitrary number used in the preferred embodiment and any suitable number may be used. If 30 consecutive beats less than a night rate have not sensed, then the device once again proceeds back up to block 117. If yes, the device proceeds to block 107, where it determines whether or not the clock 599 indicates that it is nighttime. "Nighttime" is a defined interval of the twenty-four hour clock ("day time" conversely is the rest of the twenty-four hour clock not defined as nighttime.) In the preferred embodiment nighttime is set by the physician, although in an alternate embodiment the system could also permit nighttime to be set through a patient programmer. If the clock indicates it is nighttime, then the device proceeds to night mode 109. While in night mode device stimulates the skeletal muscle graft according to a predefined schedule. In the preferred embodiment the predefined schedule during night mode 109 is a programmed set of stimulation and detection parameters for muscle stimulation. In an alternate embodiment the predefined schedule during night mode 109 may be a table of values set such that the muscle stimulation and detection parameters gradually change over time as the patient makes the transition from day to night. It should be noted that the night parameters may be set to be the same as the day rate.

Once in night mode device proceeds to determine whether the night mode has been turned off at block 111. If night mode has been turned off, then the device proceeds to the state shown at block 117. If night mode has not been turned off, then block 113 is reached, and the device determines whether or not the clock 599 indicates is daytime. If daytime is indicated, then the device proceeds to block 117. If daytime is not indicated, then the device proceeds to block 115 to determine whether 5 consecutive beats have been sensed which are greater than the daytime rate. If yes, then the block proceeds to block 117 if 5 consecutive beats greater than the daytime rate have not been sensed, then the device returns to night mode block 109. It should be understood, of course, that the use of 5 for consecutive beats greater than the daytime rate is only an arbitrary number used in the preferred embodiment and other numbers may be used. Thus, as seen in FIG. 4, the device will only proceed to night mode if the night mode has been activated, 30 consecutive beats less than a night rate have been sensed and a clock indicates it is nighttime. In addition, the day mode is reached if any of the following occur: the night mode is turned off by either the physician or patient with a programmer, the clock indicates that it is daytime or 5 consecutive beats greater than the daytime rate are sensed.

Figure 5:
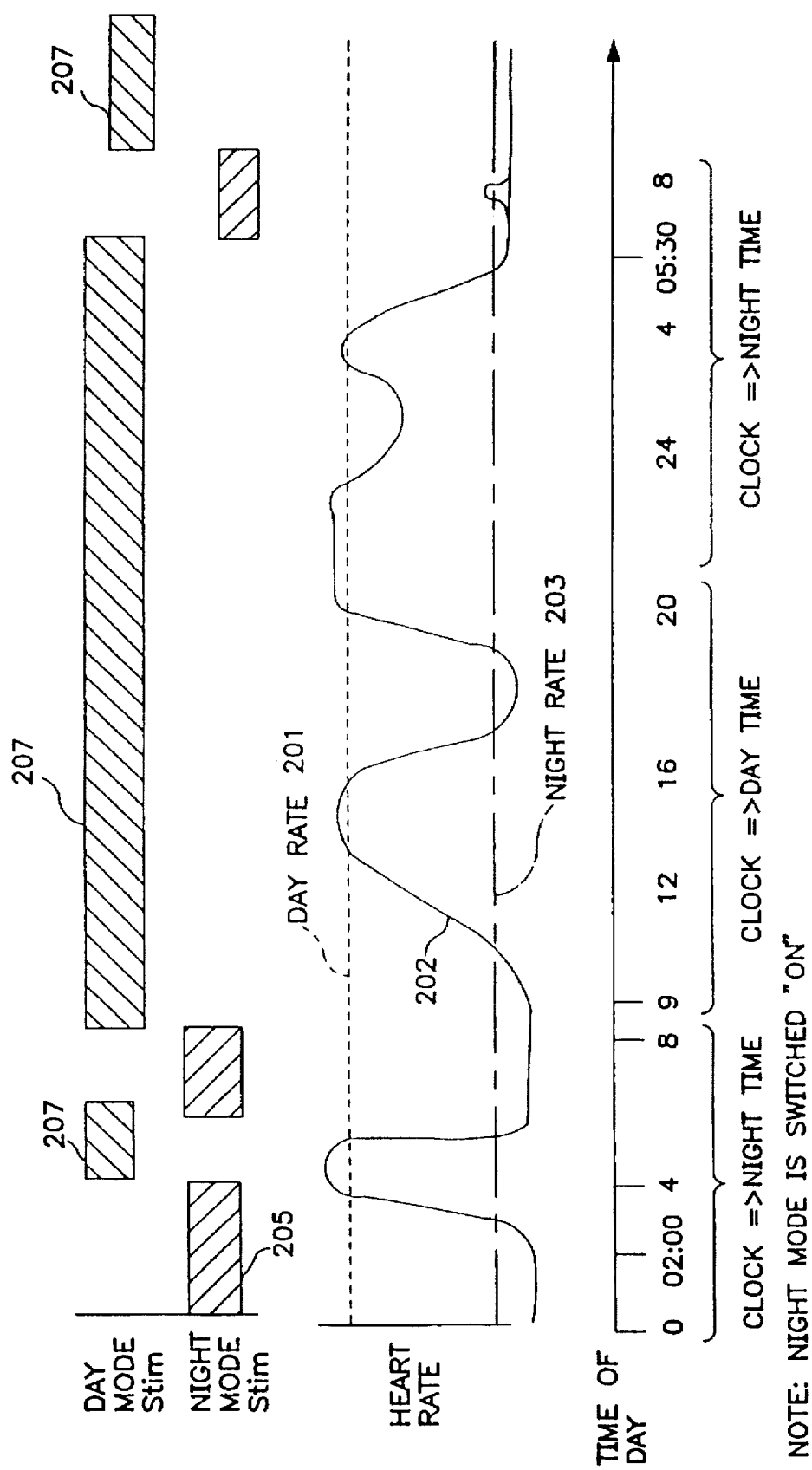
FIG. 5 is a timing diagram showing the relationship between heart rate, muscle stimulation mode and time of day according to one embodiment of the present invention.

FIG. 5 is a timing diagram showing the relationship between heart rate, muscle stimulation mode and the time of day according to a preferred embodiment of the present invention. As seen the device requires two predefined rates, day rate 201 and night rate 203. Heart rate 202 varies throughout the day, exceeding day rate 201 sometimes and less than night rate 203 at other times. As seen between 21:00 hours and 08:00 hours a clock has been set and indicates nighttime. Thus, for example, at 02:00 hours because the clock 599 indicates nighttime and heart rate 202 is less than night rate 203 and the night mode is activated, then the device would use the night mode stimulation 205. At 04:00 hours, however, because heart rate 202 has exceeded day rate 201 the night mode stimulation 205 has been replaced by day mode stimulation 207. Once heart rate 202 is less than the night rate limit for 30 consecutive beats, night mode stimulation is again reapplied, seen at here, for example, 07:00 hours.

Once clock no longer indicates nighttime, for example, at 09:00 hours, night mode stimulation 205 is no longer applied and day mode stimulation 207 is applied, even though heart rate 202 is below night rate 203. As seen, day mode stimulation 207 is applied at all times while clock indicates daytime. Once clock again indicates nighttime, an example here at 21:00 hours, night mode may again be reapplied if the conditions discussed in FIG. 4 are met. In the example of FIG. 5 night mode would not again be applied until 30 consecutive beats are experienced which are less than the night rate, seen here not occurring until approximately 05:30 hours. In the preferred embodiment night mode and day mode may be temporarily overridden by the patient. For example, if the patient desires to nap at 4:00 pm and the device is in the day mode, the patient may temporarily override day mode and set the device at night mode. The device would then continue operating in the overridden mode until reset by the patient or the mode automatically changed.

Figure 6:
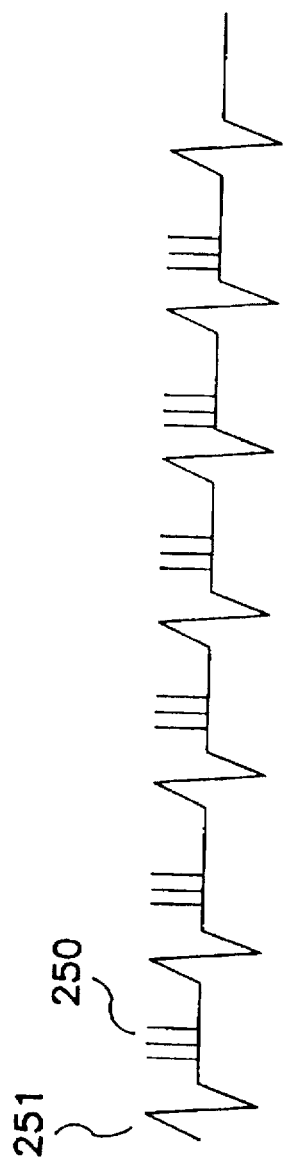
FIG. 6 depicts an example of a day mode muscle stimulation pattern.
Figure 7:
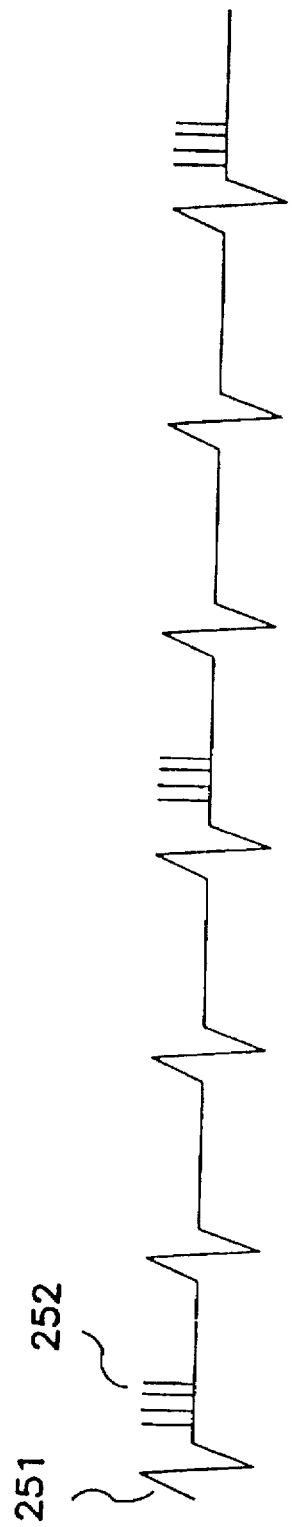
FIG. 7 depicts an example of a night mode muscle stimulation pattern.

FIG. 6 indicates one example of a day mode stimulation pattern. As seen muscle stimulation bursts 250 follows detected QRS 251 on a beat by beat basis, i.e., each QRS complex 251 is followed by a muscle stimulation burst 250. FIG. 7 depicts a night mode stimulation pattern. As seen, QRS 251 is followed by a muscle stimulation burst 252 only after every third beat. That is, the night mode stimulation synchronization ratio is 1 muscle stimulation burst for every 3 detected QRS beats. In addition it should also be noted that night mode stimulation burst 252 features a lower amplitude muscle stimulation burst as compared to day mode stimulation burst 250. Of course, other parameters, such as inter-pulse interval, burst duration, etc. as well as other synchronization ratios (e.g. 1 muscle stimulation burst for every 4, 5, 6, etc. detected QRS beats, or even no muscle stimulation at all) may also be varied between day mode and night mode and still be within the scope of the present invention.

While the present invention has been described in detail with particular reference to a preferred embodiment, it will be understood variations and modifications can be effected within the scope of the following claims. For example, although the invention preferably features two time periods throughout the twenty-four hour day, it is also conceivable the invention could be used having several time periods through the twenty-four hour day. Each of these time periods, moreover, could feature various types of muscle stimulation. A first time period, for example, could feature muscle stimulation at a first predefined ratio, amplitude and interpulse interval. A second time period, for example, could feature muscle stimulation at the first predefined ratio and amplitude but with a second interpulse interval. A third time period, for example could feature muscle stimulation at the first predefined ratio, the second interpulse interval but with a third amplitude. In short the present invention generally concerns any system which stimulates skeletal muscle with different stimulation parameters at different periods throughout the day. Variations and modifications can be imagined and still be within the scope of the following claims. Such modifications may include substituting elements or components which perform substantially the same function in substantially the same way to achieve substantially the same result for those described herein.

What is claimed:

1. A cardiac assist apparatus for assisting the mechanical contraction of a human heart, said apparatus including a surgically prepared skeletal muscle adapted to be mechanically coupled to the human heart, said apparatus comprising:

a twenty-four hour clock, the clock indicating a first time period and a second period;

means for delivering a first type of stimulation to the surgically prepared skeletal muscle when the clock indicates the first period;

means for delivering a second type of stimulation to the surgically prepared skeletal muscle when he clock indicates the second period;

wherein the means for delivering the first type of stimultion to the surgically prepared skeletal muscle comprises means for synchronizing a first burst of electrical pulses synchronized to a first number of heart beats; a wherein the means for delivering the second type of stimulation to the surgically prepared skeletal muscle comprises means for synchronizing a second burst of electrical pulses synchronized to a second number of heart beats.

2. The apparatus of claim 1 wherein the means for delivering the first type of stimulation to the surgically prepared skeletal muscle comprises means for synchronizing a first burst of electrical pulses having a first interpulse interval.

3. The apparatus of claim 1 wherein the means for delivering the second type of stimulation to the surgically prepared skeletal muscle comprises means for synchronizing a second burst of electrical pulses having a second interpulse interval.

4. A system for providing cardiac assistance, said apparatus including a surgically prepared skeletal muscle adapted to be mechanically coupled to a portion of the circulatory system, said apparatus comprising:

an implantable pulse generator adopted to be coupled to a heart and the skeletal muscle, the pulse generator further having a clock, the clock indicating either a first mode or second mode, the pulse generator having means for providing a first type of muscle stimulating pulse trains when the clock indicates the first mode and a second type of muscle stimulating pulse trains when the clock indicates the second mode; and means for synchronizing the first type of muscle stimulating pulse trains to a first number of heart beats and means for synchronizing the second type of muscle stimulating pulse trains to a second number of heart beats.

5. The system of claim 4 further comprising means for synchronizing the first type of muscle stimulating pulse trains to every second heart bean and means for synchronizing the second type of muscle stimulating pulse trains to every fourth heart beat.

6. The system of claim 4 wherein the first type of muscle stimulating pulse trains are synchronized to every third heart beat and the second type of muscle stimulating pulse trains are synchronized to every fifth beat.

7. The system of claim 4 wherein the clock is a twenty-four hour clock.

* * * * *